United States Patent
Anukhin et al.

(10) Patent No.: US 8,974,514 B2
(45) Date of Patent: Mar. 10, 2015

(54) INTRAVASCULAR STENT WITH INTEGRATED LINK AND RING STRUT

(75) Inventors: Boris Anukhin, San Jose, CA (US); Hao-Ming Hsiao, Cupertino, CA (US); Keif Fitzgerald, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1075 days.

(21) Appl. No.: 11/724,089

(22) Filed: Mar. 13, 2007

(65) Prior Publication Data

US 2008/0228261 A1 Sep. 18, 2008

(51) Int. Cl.
*A61F 2/06* (2013.01)
*A61F 2/915* (2013.01)

(52) U.S. Cl.
CPC ....... *A61F 2/915* (2013.01); *A61F 2002/91541* (2013.01); *A61F 2002/91583* (2013.01); *A61F 2250/0036* (2013.01); *A61F 2230/0054* (2013.01)
USPC ...................................................... 623/1.15

(58) Field of Classification Search
USPC ....................................... 623/1.16, 1.28, 1.15
See application file for complete search history.

(56) References Cited

U.S. PATENT DOCUMENTS

| | | |
|---|---|---|
| 4,733,665 A | 3/1988 | Palmaz |
| 4,739,762 A | 4/1988 | Palmaz |
| 4,740,207 A | 4/1988 | Kreamer |
| 4,776,337 A | 10/1988 | Palmaz |
| 5,007,926 A | 4/1991 | Derbyshire |
| 5,167,614 A | 12/1992 | Tessman et al. |
| 5,192,307 A | 3/1993 | Wall |
| 5,411,549 A | 5/1995 | Peters |
| 5,421,955 A | 6/1995 | Lau et al. |
| 5,423,885 A | 6/1995 | Williams |
| 5,441,515 A | 8/1995 | Khosravi et al. |
| 5,443,458 A | 8/1995 | Eury |
| 5,443,500 A | 8/1995 | Sigwart |
| 5,514,154 A * | 5/1996 | Lau et al. ..................... 623/1.15 |
| 5,549,662 A | 8/1996 | Fordenbacher |
| 5,556,413 A | 9/1996 | Lam |
| 5,569,295 A | 10/1996 | Lam |
| 5,593,417 A | 1/1997 | Rhodes |

(Continued)

FOREIGN PATENT DOCUMENTS

| | | |
|---|---|---|
| DE | 10050970 A1 | 11/2002 |
| EP | 1 477 135 B1 | 4/2007 |
| WO | 0062710 A1 | 10/2000 |

*Primary Examiner* — Thomas McEvoy
*Assistant Examiner* — Julie A Szpira
(74) *Attorney, Agent, or Firm* — Jonathan D. Feuchtwing; Fulwider Patton LLP

(57) ABSTRACT

An expandable stent is implanted in a body lumen, such as a coronary artery, peripheral artery, or other body lumen. The stent includes a plurality of rings connected by links. The stent has a high degree of flexibility in the longitudinal direction, yet has adequate vessel wall coverage and radial strength sufficient to hold open an artery or other body lumen. The stent can be compressed or crimped onto a catheter to a very low profile since links are integrally formed from a portion of the struts forming the rings. The stent is constructed so that the cylindrical rings are very close together in order to provide maximum scaffolding, and if the stent has a drug coating, to provide a uniform drug delivery over the length of the stent. The connecting links are integrally formed from a portion of the struts forming the rings so that the links can have a maximum length thereby providing increased longitudinal flexibility of the stent.

31 Claims, 13 Drawing Sheets

(56) References Cited

U.S. PATENT DOCUMENTS

| | | |
|---|---|---|
| 5,593,434 A | 1/1997 | Williams |
| 5,603,721 A | 2/1997 | Lau et al. |
| 5,643,314 A | 7/1997 | Carpenter et al. |
| 5,728,158 A | 3/1998 | Lau et al. |
| 5,733,303 A | 3/1998 | Israel et al. |
| 5,735,893 A | 4/1998 | Lau et al. |
| 5,759,192 A | 6/1998 | Saunders |
| 5,766,238 A | 6/1998 | Lau et al. |
| 5,772,864 A | 6/1998 | Moller et al. |
| 5,776,161 A | 7/1998 | Globerman |
| 5,780,807 A | 7/1998 | Saunders |
| 5,797,951 A | 8/1998 | Mueller |
| 5,807,404 A | 9/1998 | Richter |
| 5,817,126 A | 10/1998 | Imran |
| 5,843,120 A | 12/1998 | Israel et al. |
| 5,843,164 A | 12/1998 | Frantzen et al. |
| 5,853,419 A | 12/1998 | Imran |
| 5,868,782 A | 2/1999 | Frantzen |
| 5,876,432 A | 3/1999 | Lau et al. |
| 5,919,225 A | 7/1999 | Lau et al. |
| 5,938,682 A | 8/1999 | Hojeibane et al. |
| 6,015,429 A | 1/2000 | Lau et al. |
| 6,033,433 A | 3/2000 | Ehr et al. |
| 6,042,597 A | 3/2000 | Kveen et al. |
| 6,056,776 A | 5/2000 | Lau et al. |
| 6,059,808 A | 5/2000 | Boussignac et al. |
| 6,059,810 A | 5/2000 | Brown et al. |
| 6,063,101 A | 5/2000 | Jacobsen et al. |
| 6,066,167 A | 5/2000 | Lau et al. |
| 6,066,168 A | 5/2000 | Lau et al. |
| 6,066,169 A * | 5/2000 | McGuinness .............. 623/1.16 |
| 6,103,320 A | 8/2000 | Matsumoto et al. |
| 6,120,847 A | 9/2000 | Yang et al. |
| 6,124,523 A | 9/2000 | Banas et al. |
| 6,129,755 A * | 10/2000 | Mathis et al. ............. 623/1.15 |
| 6,270,524 B1 | 8/2001 | Kim |
| 6,293,966 B1 | 9/2001 | Frantzen |
| 6,309,412 B1 | 10/2001 | Lau et al. |
| 6,309,414 B1 | 10/2001 | Rolando |
| 6,312,463 B1 | 11/2001 | Rourke et al. |
| 6,325,821 B1 | 12/2001 | Gaschino et al. |
| 6,325,826 B1 | 12/2001 | Vardi et al. |
| 6,331,190 B1 | 12/2001 | Shokoohi et al. |
| 6,334,870 B1 | 1/2002 | Ehr et al. |
| 6,334,871 B1 | 1/2002 | Dor et al. |
| 6,336,938 B1 | 1/2002 | Kavteladze et al. |
| 6,355,058 B1 | 3/2002 | Pacetti et al. |
| 6,387,123 B1 | 5/2002 | Jacobs et al. |
| 6,432,133 B1 | 8/2002 | Lau et al. |
| 6,451,049 B2 | 9/2002 | Vallana et al. |
| 6,461,380 B1 | 10/2002 | Cox |
| 6,475,236 B1 | 11/2002 | Roubin et al. |
| 6,485,508 B1 | 11/2002 | McGuinness |
| 6,503,272 B2 | 1/2003 | Duerig et al. |
| 6,506,211 B1 | 1/2003 | Skubitz et al. |
| 6,540,774 B1 | 4/2003 | Cox |
| 6,605,110 B2 | 8/2003 | Harrison |
| 6,613,079 B1 | 9/2003 | Wolinsky et al. |
| 6,673,106 B2 | 1/2004 | Mitelberg et al. |
| 6,689,159 B2 | 2/2004 | Lau et al. |
| 6,699,278 B2 | 3/2004 | Fischell et al. |
| 6,709,454 B1 | 3/2004 | Cox et al. |
| 6,730,116 B1 | 5/2004 | Wolinsky et al. |
| 6,846,323 B2 | 1/2005 | Yip et al. |
| 6,866,805 B2 * | 3/2005 | Hong et al. .................. 264/161 |
| 6,896,695 B2 | 5/2005 | Mueller et al. |
| 6,896,696 B2 | 5/2005 | Doran et al. |
| 6,896,697 B1 | 5/2005 | Yip et al. |
| 6,896,698 B2 | 5/2005 | Rolando et al. |
| 6,896,699 B2 | 5/2005 | Wilson et al. |
| 6,899,729 B1 | 5/2005 | Cox et al. |
| 6,908,479 B2 | 6/2005 | Lau et al. |
| 6,908,480 B2 | 6/2005 | Jayaraman |
| 6,929,657 B2 | 8/2005 | Gomez et al. |
| 6,929,658 B1 | 8/2005 | Freidberg et al. |
| 6,929,660 B1 * | 8/2005 | Ainsworth et al. .......... 623/1.15 |
| 6,939,373 B2 | 9/2005 | Gomez et al. |
| 6,942,689 B2 | 9/2005 | Majercak |
| 6,942,690 B1 | 9/2005 | Pollock et al. |
| 6,945,993 B2 | 9/2005 | Kveen et al. |
| 6,955,686 B2 | 10/2005 | Majercak et al. |
| 6,962,604 B2 | 11/2005 | Hijlkema |
| 6,964,680 B2 | 11/2005 | Shanley |
| 6,969,401 B1 | 11/2005 | Marotta et al. |
| 6,969,402 B2 | 11/2005 | Bales et al. |
| 6,976,993 B2 | 12/2005 | Schaldach et al. |
| 6,979,347 B1 | 12/2005 | Wu et al. |
| 6,979,349 B1 | 12/2005 | Dang et al. |
| 6,997,944 B2 | 2/2006 | Harrison et al. |
| 6,997,946 B2 | 2/2006 | Girton et al. |
| 7,004,968 B2 | 2/2006 | Lootz et al. |
| D516,723 S | 3/2006 | Shanley |
| 7,014,654 B2 | 3/2006 | Welsh et al. |
| 7,018,403 B1 | 3/2006 | Pienknagura |
| 7,025,777 B2 | 4/2006 | Moore |
| 7,029,492 B1 | 4/2006 | Mitsudou et al. |
| 7,029,493 B2 | 4/2006 | Majercak et al. |
| 7,060,090 B2 | 6/2006 | Thornton |
| 7,070,614 B1 | 7/2006 | Neuss et al. |
| 7,081,130 B2 | 7/2006 | Jang |
| 7,090,694 B1 | 8/2006 | Morris et al. |
| 7,094,255 B2 | 8/2006 | Penn et al. |
| 7,105,018 B1 | 9/2006 | Yip et al. |
| 7,112,216 B2 | 9/2006 | Gregorich |
| 7,118,593 B2 | 10/2006 | Davidson et al. |
| 7,122,049 B2 | 10/2006 | Banas et al. |
| 7,131,993 B2 * | 11/2006 | Gregorich ................... 623/1.16 |
| 7,135,038 B1 * | 11/2006 | Limon ......................... 623/1.15 |
| 7,147,661 B2 | 12/2006 | Chobotov et al. |
| 7,169,174 B2 | 1/2007 | Fischell et al. |
| 7,169,175 B2 | 1/2007 | Cottone, Jr. et al. |
| 7,179,285 B2 | 2/2007 | Ikeuchi et al. |
| 7,179,286 B2 * | 2/2007 | Lenz ............................ 623/1.15 |
| 7,195,640 B2 | 3/2007 | Falotico et al. |
| 7,195,646 B2 | 3/2007 | Nahleili |
| 7,204,848 B1 | 4/2007 | Brown et al. |
| 7,208,009 B2 | 4/2007 | Richter |
| 7,208,010 B2 | 4/2007 | Shanley et al. |
| 2001/0037146 A1 | 11/2001 | Lau et al. |
| 2001/0037147 A1 | 11/2001 | Lau et al. |
| 2001/0047200 A1 | 11/2001 | White et al. |
| 2001/0047201 A1 | 11/2001 | Cox et al. |
| 2001/0056298 A1 | 12/2001 | Brown et al. |
| 2002/0007209 A1 | 1/2002 | Scheerder et al. |
| 2002/0016623 A1 | 2/2002 | Kula et al. |
| 2002/0042648 A1 * | 4/2002 | Schaldach et al. ........... 623/1.15 |
| 2002/0042649 A1 | 4/2002 | Schaldach et al. |
| 2002/0045935 A1 | 4/2002 | Jang |
| 2002/0055770 A1 | 5/2002 | Doran et al. |
| 2002/0072793 A1 | 6/2002 | Rolando et al. |
| 2002/0123798 A1 | 9/2002 | Burgermeister |
| 2002/0156523 A1 | 10/2002 | Lau et al. |
| 2002/0183831 A1 | 12/2002 | Rolando et al. |
| 2003/0004567 A1 | 1/2003 | Boyle et al. |
| 2003/0014102 A1 * | 1/2003 | Hong et al. .................. 623/1.15 |
| 2003/0083646 A1 | 5/2003 | Sirhan et al. |
| 2003/0105515 A1 | 6/2003 | Skubitz et al. |
| 2003/0149469 A1 * | 8/2003 | Wolinsky et al. ............ 623/1.11 |
| 2004/0054399 A1 | 3/2004 | Roth |
| 2004/0127970 A1 * | 7/2004 | Saunders et al. ............ 623/1.15 |
| 2004/0172128 A1 * | 9/2004 | Hong et al. .................. 623/1.16 |
| 2007/0050011 A1 * | 3/2007 | Klein et al. .................. 623/1.16 |
| 2008/0051878 A1 * | 2/2008 | Cheng et al. ................ 623/1.16 |

* cited by examiner

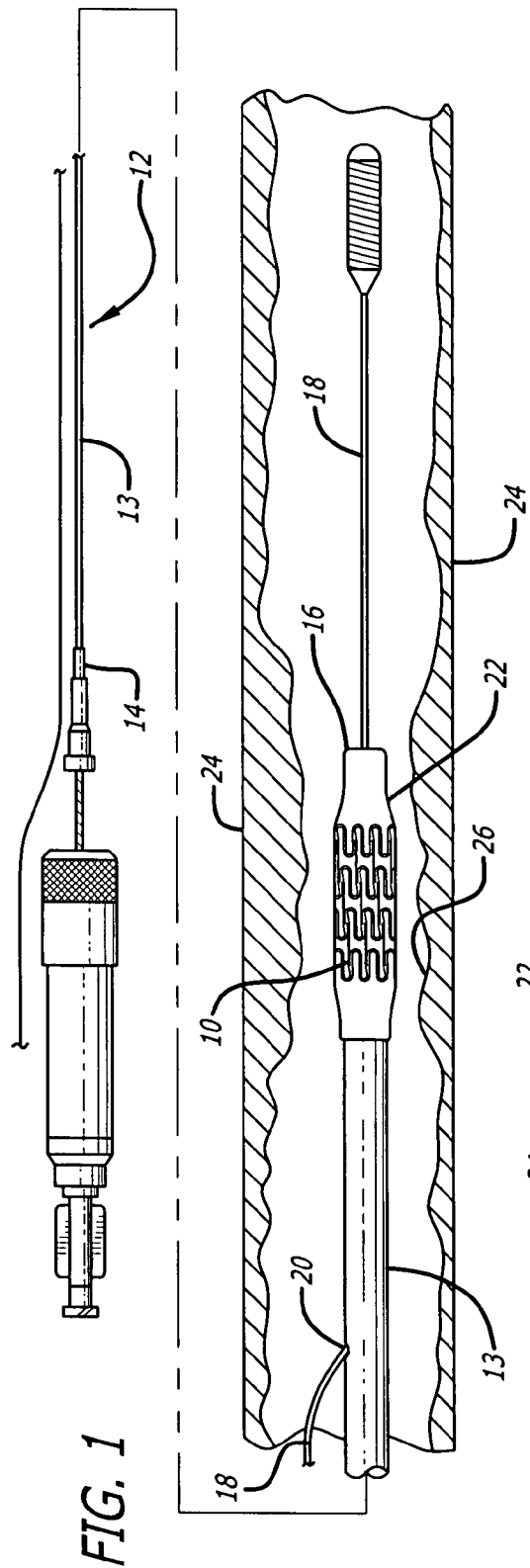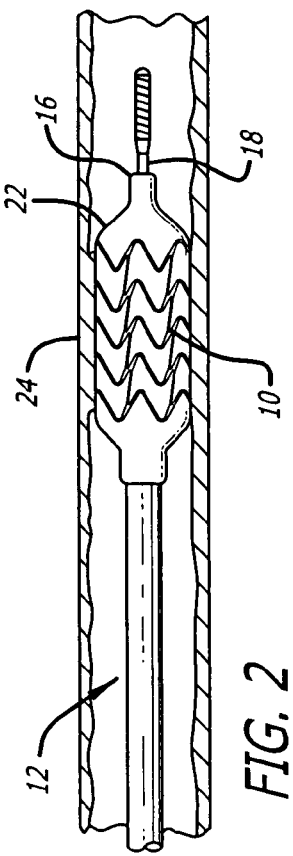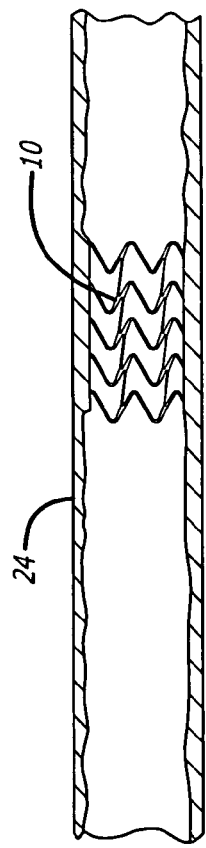

INTRAVASCULAR STENT WITH INTEGRATED LINK AND RING STRUT

BACKGROUND OF THE INVENTION

The invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. For example, prior art stents have multiple cylindrical rings connected by one or more straight or undulating links. While some of these stents are flexible and have the appropriate radial rigidity needed to hold open a vessel or artery, there typically is a tradeoff between flexibility and radial strength and the ability to tightly compress or crimp the stent onto a catheter so that it does not move relative to the catheter or dislodge prematurely prior to controlled implantation in a vessel.

What has been needed and heretofore unavailable is a stent which has a high degree of flexibility so that it can be advanced through tortuous passageways and can be readily expanded, and yet have the mechanical strength to hold open the body lumen or artery into which it is implanted and provide adequate vessel wall coverage. The present invention satisfies this need. That is, the stent of the present invention has a high degree of compressibility to secure it on the catheter and provide a low profile and a high degree of flexibility making it possible to advance the stent easily through tortuous arteries, yet the stent has sufficient radial rigidity so that it can hold open an artery or other blood vessel, or tack up a dissected lining and provide adequate vessel wall coverage.

SUMMARY OF THE INVENTION

The present invention is directed to an intravascular stent that has a pattern or configuration that permits the stent to be tightly compressed or crimped onto a catheter to provide an extremely low profile and to prevent relative movement between the stent and the catheter. The stent also is highly flexible along its longitudinal axis to facilitate delivery through tortuous body lumens, but which is stiff and stable enough radially in its expanded condition to maintain the patency of a body lumen such as an artery when the stent is implanted therein.

The stent of the present invention generally includes a plurality of rings that are interconnected to form the stent. In one embodiment, links are integrally formed from struts in the rings to connect adjacent rings. In one aspect of the invention, the space between adjacent rings is minimized to increase scaffolding while the length of connecting links is lengthened to increase flexibility. The stent typically is mounted on a balloon catheter if it is balloon expandable or mounted on or in a catheter without a balloon if it is self-expanding.

Each of the rings making up the stent have a proximal end and a distal end and a cylindrical plane defined by a cylindrical outer wall surface that extends circumferentially between the proximal end and the distal end of the ring. Generally the rings have a serpentine or undulating shape which includes at least one U-shaped or V-shaped element, and typically each ring has more than one U-shaped or V-shaped element. The rings are interconnected by at least one link which attaches one ring to an adjacent ring. The links are highly flexible and allow the stent to be highly flexible along its longitudinal axis. In one embodiment, the links have a bend or curved portion and a straight portion. At least a portion of the links is formed from a portion of a strut in the rings.

In one embodiment, the stent of the present invention includes a tubular member having rings spaced apart along a longitudinal axis. The rings have curved portions that are connected by first struts or second struts. The rings are connected by links where a portion of the links are integrally formed from a portion of the second struts. In other words, the second struts have a bar arm and a link arm. The bar arm connects to a peak while the link arm connects to a portion of the link. More specifically, the second strut has a gap between the bar arm and the link arm so that the link arm can flexibly connect one ring to an adjacent ring. In another embodiment, the link has one or more bends or curved portions to further enhance flexibility of the link.

In another embodiment, the stent is self-expanding and has links that have an S-shaped portion that expands as the stent expands when implanted. Since the stent is formed from a superelastic alloy, the S-shaped portion of the link lengthens to compensate for any shortening of the rings when the stent self expands so that the overall length of the stent remains substantially the same from the crimped or compressed configuration to the expanded, implanted configuration.

Not only do the links that interconnect the rings provide flexibility to the stent, but the positioning of the links also enhances the flexibility by allowing uniform flexibility when the stent is bent in any direction along its longitudinal axis. Uniform flexibility along the stent derives in part from the links of one ring being circumferentially offset from the links in an adjacent ring. Further, the rings are configured to provide flexibility to the stent in that portions of the rings can flex or bend as the stent is delivered through a tortuous vessel.

In one embodiment, the rings are formed of a plurality of peaks or crests where the peaks of one ring are circumferentially offset from the peaks of an adjacent ring. In this configuration, at least one link attaches each ring to an adjacent ring so that at least a portion of the link is positioned within one of the peaks and it attaches the peaks to an adjacent peak.

While the cylindrical rings and undulating links generally are not separate structures, they have been conveniently referred to as rings and links for ease of identification. Further, the cylindrical rings can be thought of as comprising a series of U-shaped structures in a repeating pattern. Again, while the rings are not divided up or segmented into U-shaped structures, the pattern of the rings resemble such configuration. The U-shaped structures promote flexibility in the stent primarily by flexing as the stent is delivered through a tortuous vessel.

The number and location of links that interconnect adjacent rings can be varied as the application requires. In one embodiment, the links have a bend or curved portion that will expand when the cylindrical rings of the stent expand radially outwardly. When the links expand the overall length of the stent remains unchanged as the stent rings expand. In other words, the stent does not foreshorten because the bends in links open in the longitudinal direction to compensate for any foreshortening of the radially expanding rings. Typically, this embodiment includes self-expanding stents formed of superelastic alloys such as nitinol and the like. As used throughout the present application, the term adjacent may be used to define directly adjacent or indirectly adjacent.

The rings of the stent may be plastically deformed when expanded when the stent is made from a metal that is balloon expandable. Typically, the balloon-expandable stent is made from a stainless steel or cobalt-chromium alloy, multi-layer materials or other similar biocompatible materials.

Similarly, if the rings are constructed of a superelastic alloy, the rings of the stent may expand radially outwardly upon the removal of a restraining member. Examples of superelastic alloys, are nickel-titanium (NiTi) alloys.

Because of the configuration of the links, the stent has a high degree of flexibility along the stent axis, which reduces the tendency of stent fishscaling. Stent fishscaling can occur when the stent is bent and portions of the stent project outward when the stent is in the unexpanded condition. The present invention links reduce the likelihood of fishscaling.

Further, because of the positioning of the links, and the fact that the undulating links expand or stretch when the stent is radially expanded, the overall length of the stent is substantially the same in the unexpanded and expanded configurations. In other words, the stent will not substantially shorten upon expansion.

The stent may be formed from a tube by laser cutting the pattern of rings and links in the tube. The stent also may be formed by laser cutting a flat metal sheet in the pattern of the rings and links, and then rolling the pattern into the shape of the tubular stent and providing a longitudinal weld to form the stent.

BRIEF DESCRIPTION OF THE DRAWINGS

FIG. 1 is an elevational view, partially in section, of the stent mounted on a rapid-exchange delivery catheter and positioned within an artery.

FIG. 2 is an elevational view, partially in section, similar to that shown in FIG. 1 wherein the stent is expanded within the artery, so that the stent embeds within the arterial wall.

FIG. 3 is an elevational view, partially in section, showing the expanded stent implanted within the artery after withdrawal of the rapid-exchange delivery catheter.

DETAILED DESCRIPTION OF THE PREFERRED EMBODIMENTS

Figure 4:
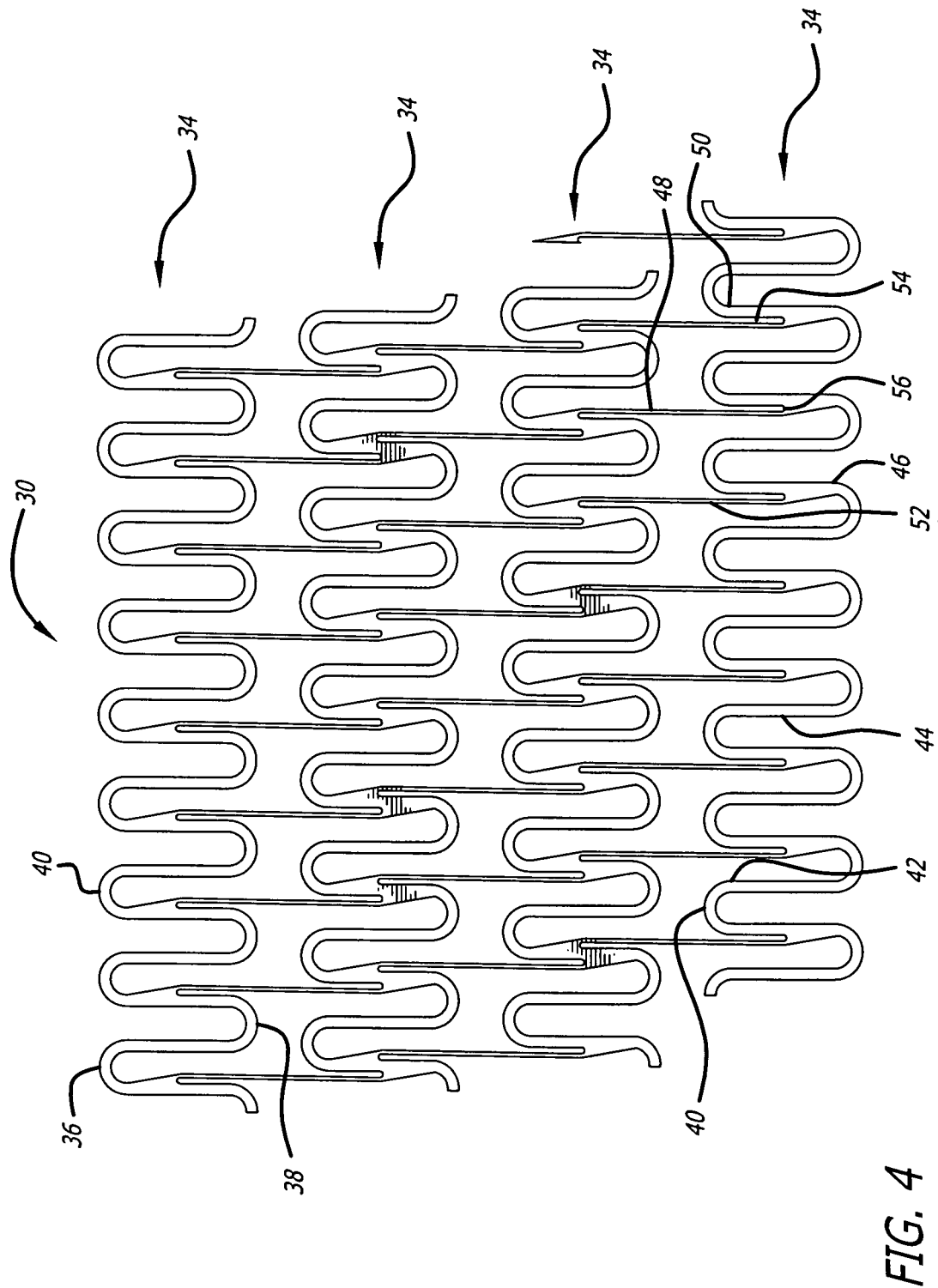
FIG. 4 is a plan view of a flattened stent which illustrates the unexpanded pattern of the stent shown in FIGS. 1-3.
Figure 5:
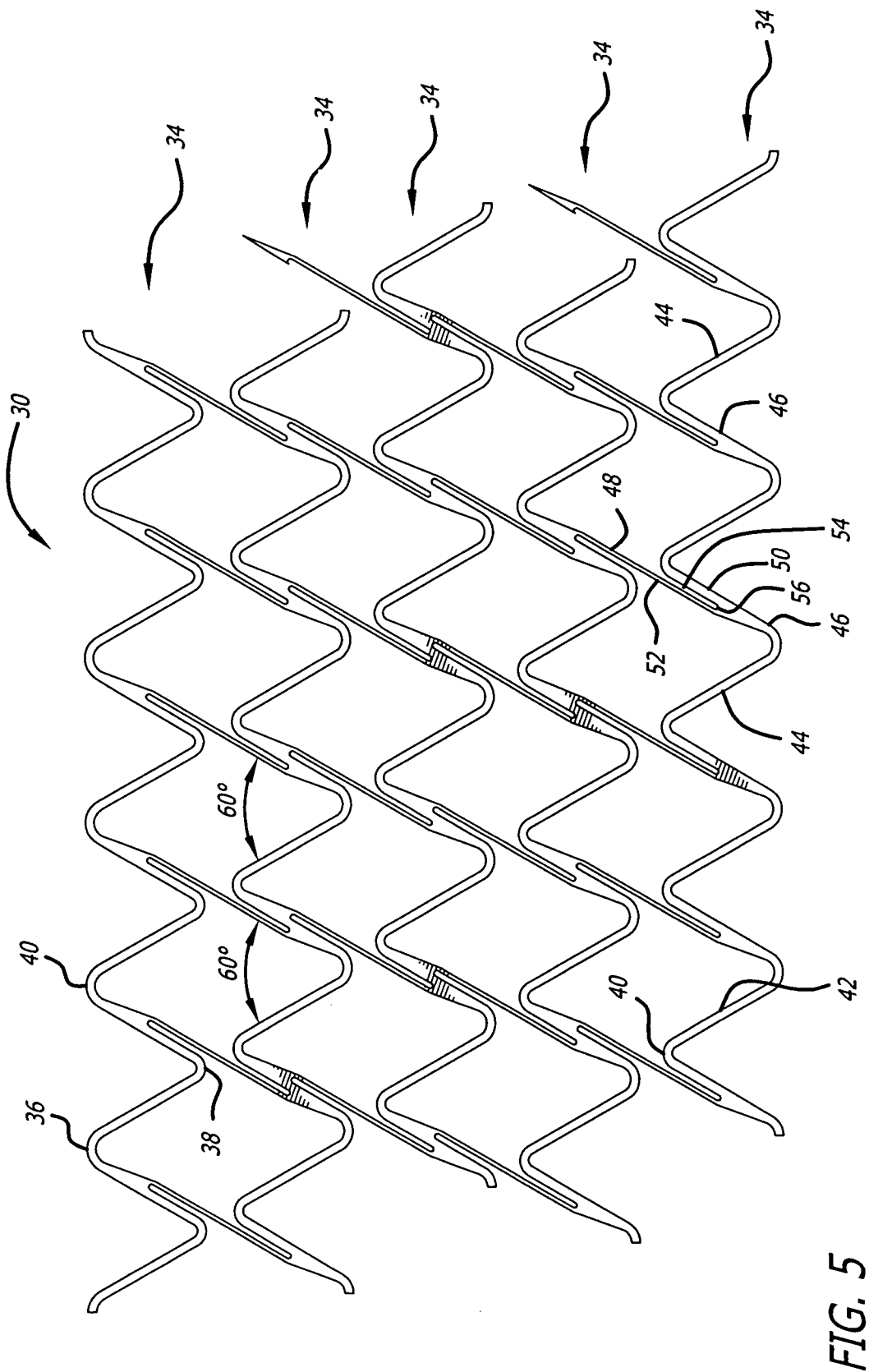
FIG. 5 is a plan view of the stent of FIG. 4 in a partially expanded state.

The present invention stent improves on existing stents by providing a longitudinally flexible stent having a uniquely designed pattern and novel interconnecting members. In addition to providing longitudinal flexibility, the stent of the present invention also provides radial rigidity and a high degree of scaffolding of a vessel wall, such as a coronary artery. The design of the highly flexible interconnecting members and their placement relative to an adjacent U-shaped member provides for a tightly compressed stent onto a catheter while maintaining a high degree of flexibility during delivery.

Turning to the drawings, FIG. 1 depicts a stent 10 of the present invention mounted on a conventional catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the coronary arteries (or other vessels).

As shown in FIG. 1, a partial cross-section of an artery 24 is shown with a small amount of plaque that has been previously treated by an angioplasty or other repair procedure. Stent 10 is used to repair a diseased or damaged arterial wall which may include the plaque 26 as shown in FIG. 1, or a dissection, or a flap which are sometimes found in the coronary arteries, peripheral arteries and other vessels.

In a typical procedure to implant a balloon expandable stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent 10 expanded and pressed against the vessel wall, and in FIG. 3, the implanted stent 10 remains in the vessel after the balloon has been deflated and the catheter assembly and guide wire have been withdrawn from the patient. If the stent 10 is self-expanding, it can be delivered by several well known methods. The self-expanding stent can be compressed into a catheter where it remains until it is delivered at the target site by pushing the stent out of the catheter where it then self-expands into the vessel. The self-expanding stent also can be compressed onto a catheter or a balloon catheter and held in place by a sheath over the stent. When the sheath is retracted, the stent will self-expand into the vessel. A balloon catheter can be used to post-dilate the self-expanding embodiment stent.

The stent 10 serves to old open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced rings at regular intervals provide uniform support for the wall of the artery, and consequently are well adapted to tack up and hold in place small flaps or dissections in the wall of the artery, as illustrated in FIGS. 2 and 3.

Figure 9:
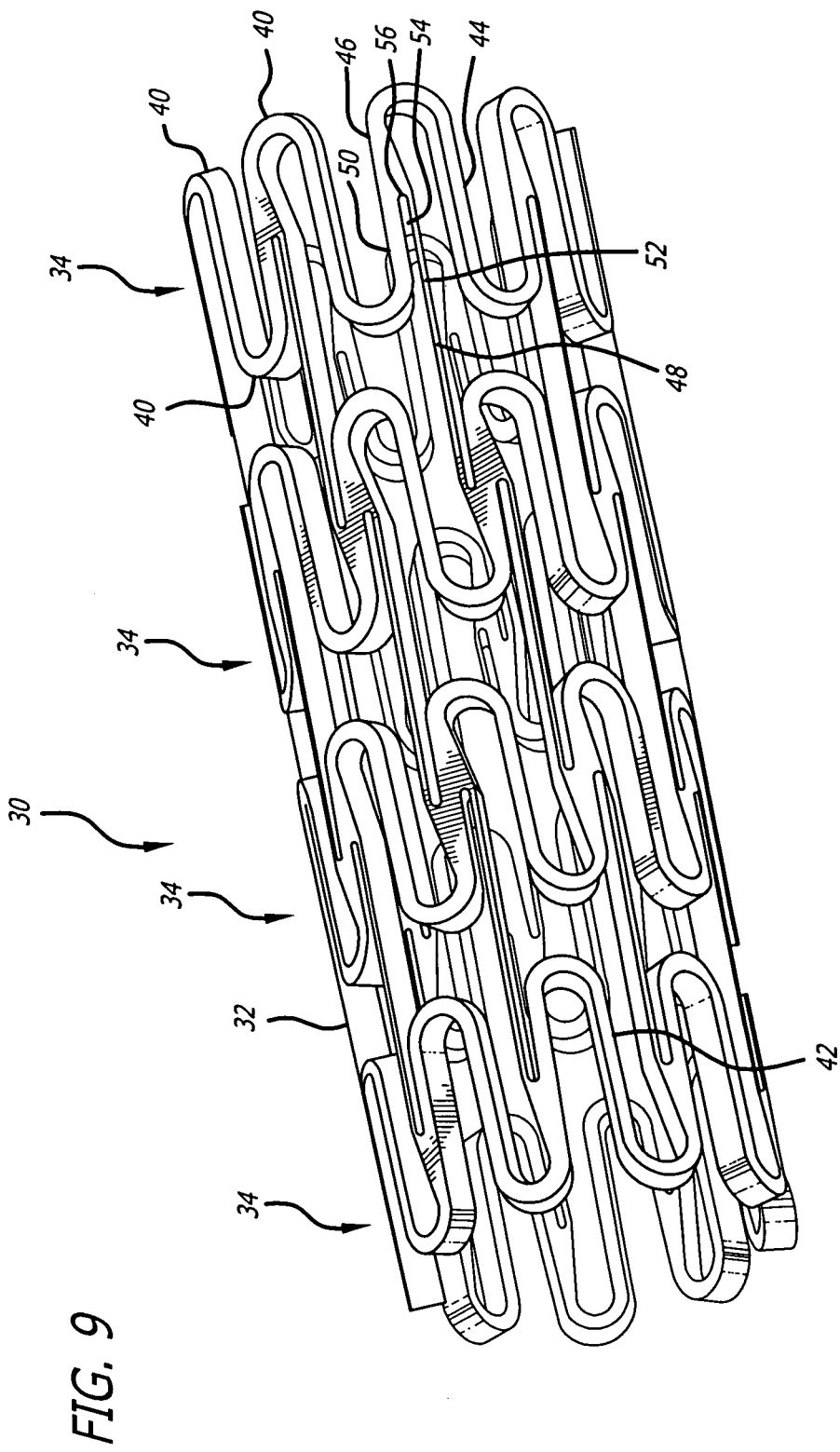
FIG. 9 is a perspective view of the stent of FIG. 4 in a cylindrical configuration and is tightly crimped or compressed.
Figure 10:
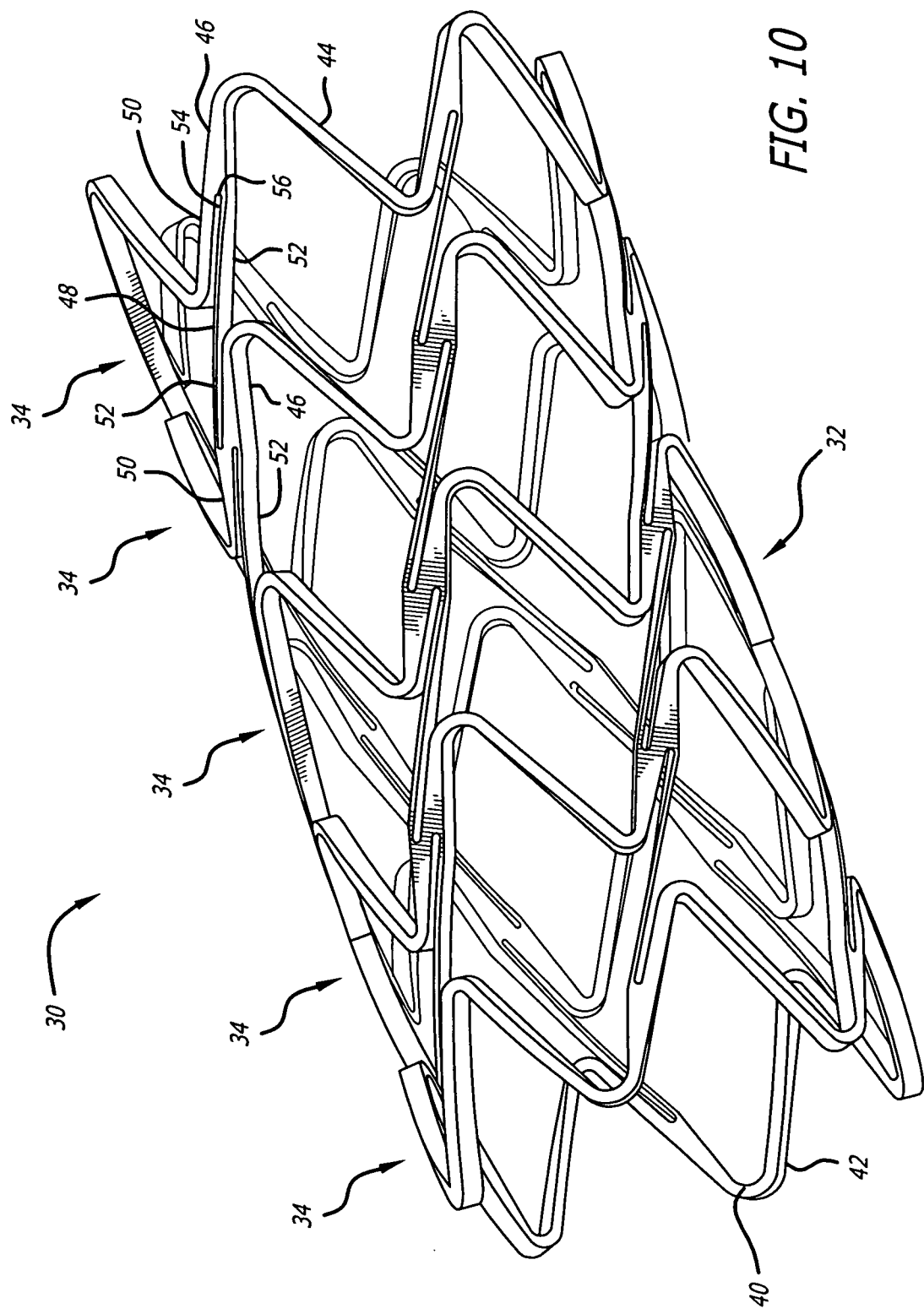
FIG. 10 is a perspective view of the stent of FIG. 4 in a partially expanded configuration.

In keeping with the present invention, FIGS. 4-17 depict the stent in various embodiments. Referring to FIG. 4, for example, stent 30 is shown in a flattened condition so that the pattern can be clearly viewed, even though the stent is in a cylindrical form in use, such as shown in FIG. 9. The stent is typically formed from a tubular member, however, it can be formed from a flat sheet such as shown in FIG. 4 and rolled into a cylindrical configuration as shown in FIG. 9.

Figure 6:
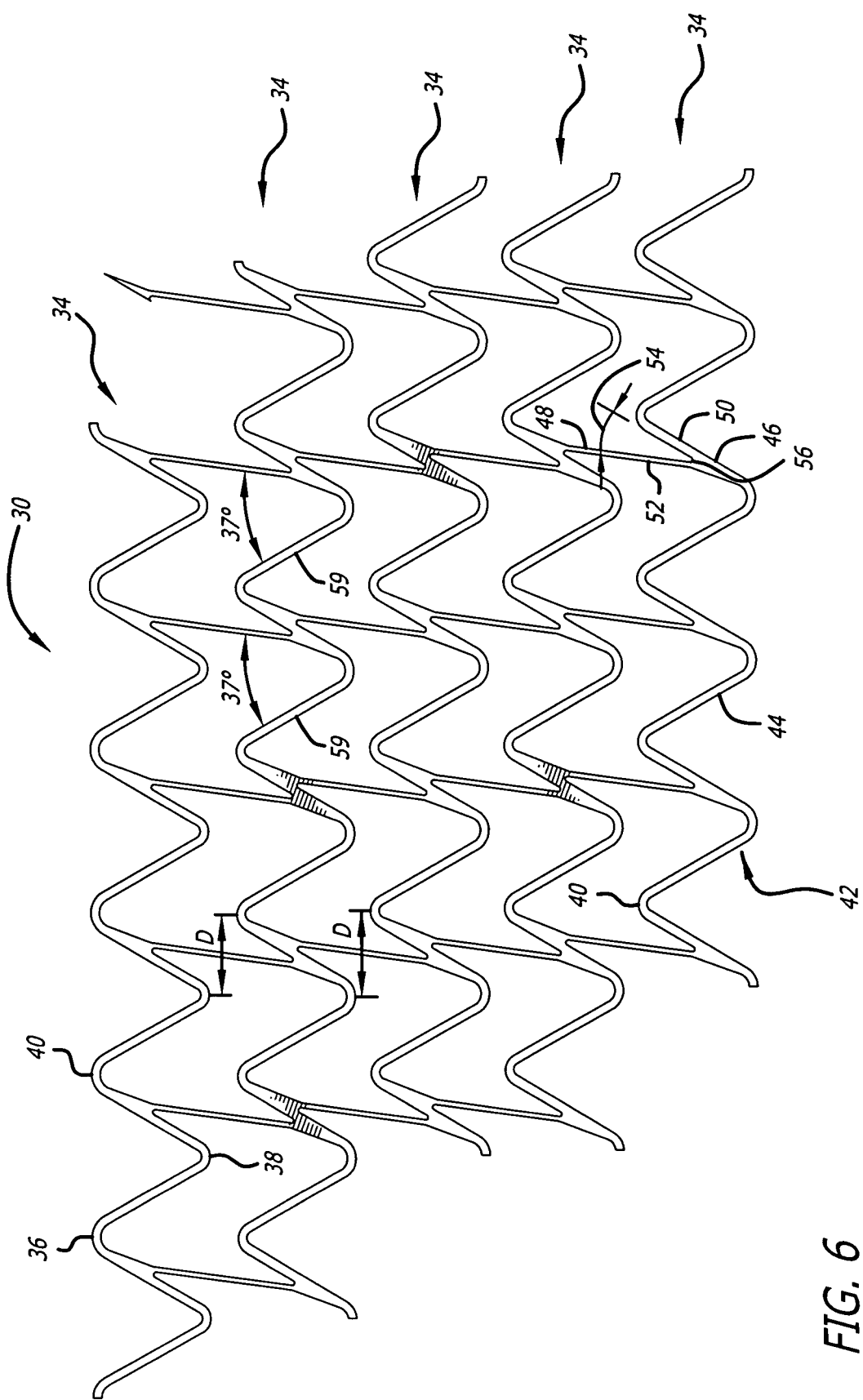
FIG. 6 is a plan view of a stent having superelastic properties in an expanded configuration.
Figure 7:
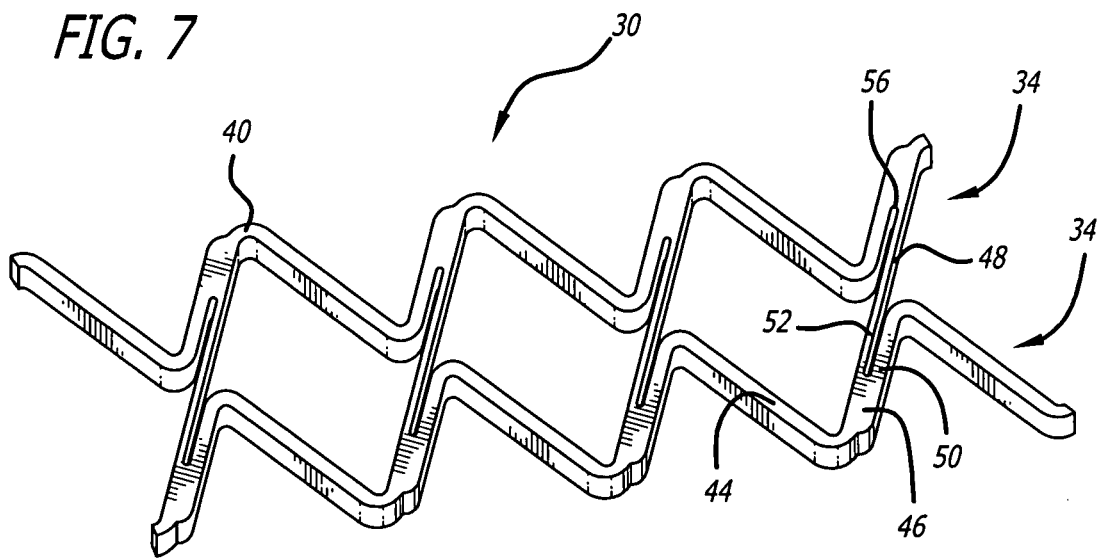
FIG. 7 is a plan view of a portion of the stent of FIG. 4.
Figure 8:
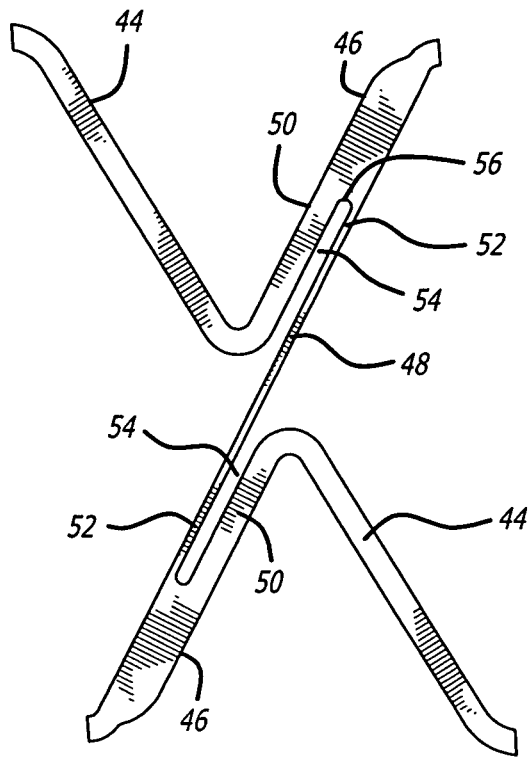
FIG. 8 is a plan view of an enlarged portion of the stent of FIG. 4.
Figure 11:
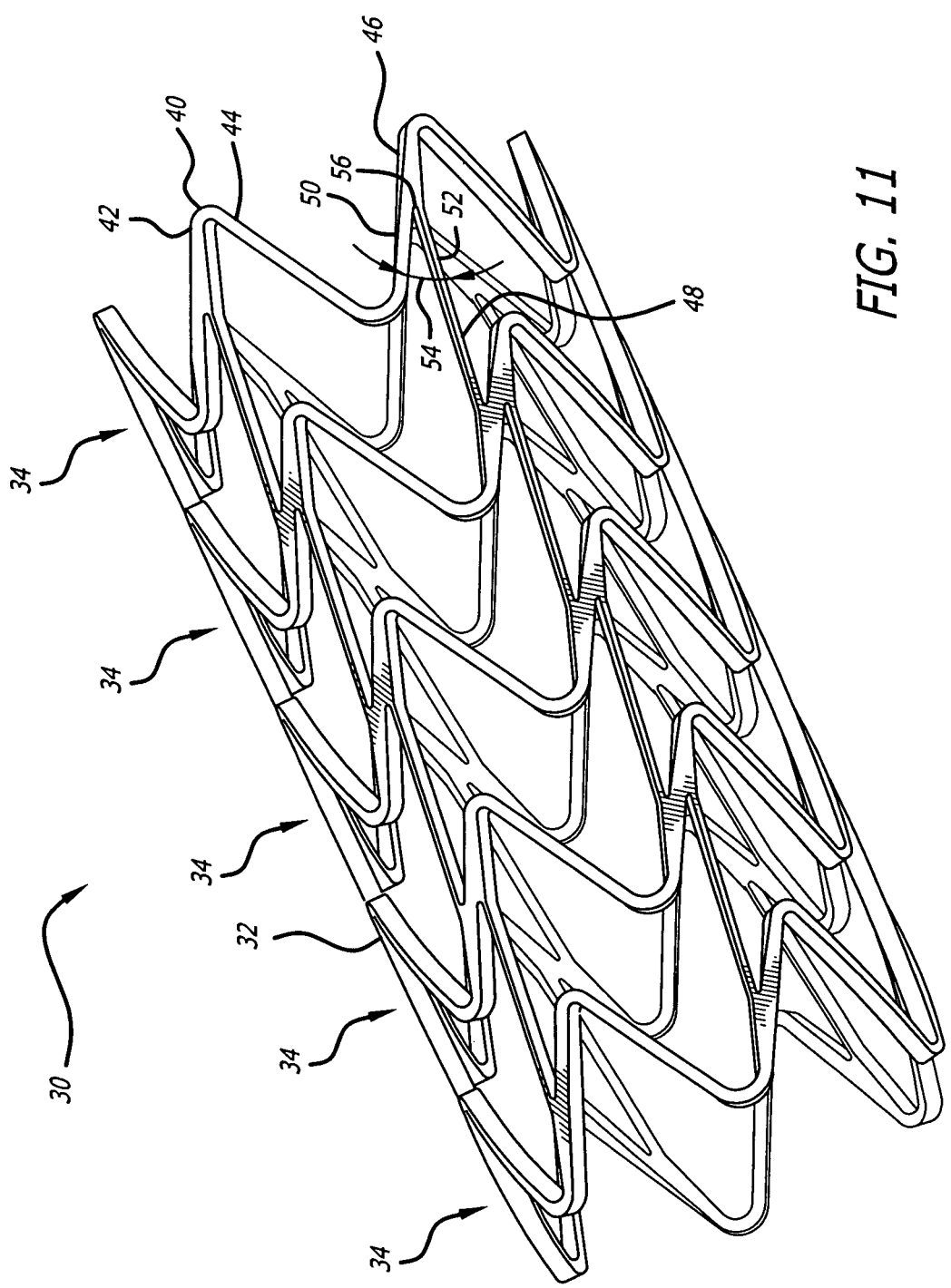
FIG. 11 is a perspective view of the stent of FIG. 4 in a fully expanded configuration.
Figure 12:
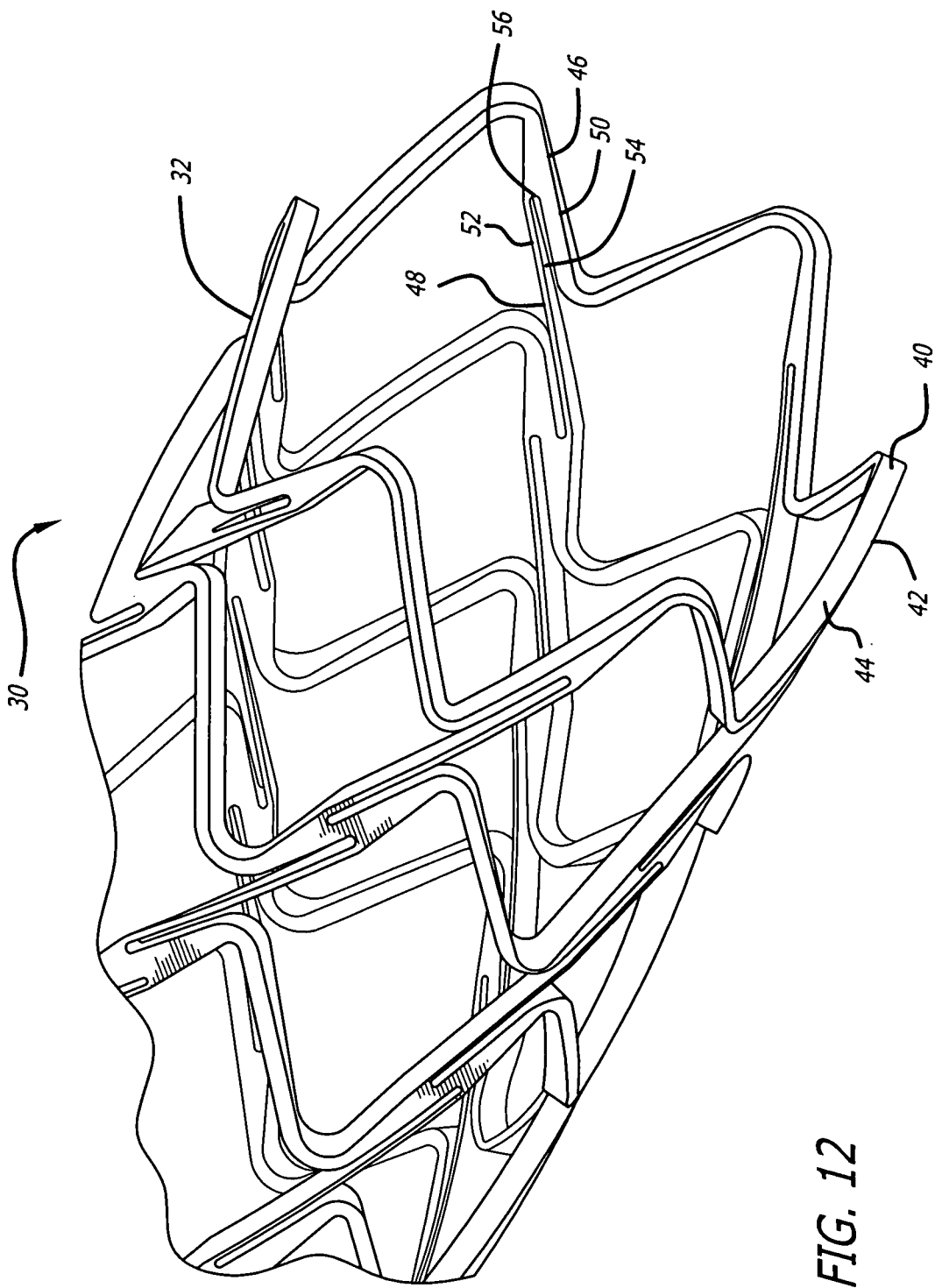
FIG. 12 is a partial perspective view of a photomycrograph of the stent of FIG. 4 in a partially expanded configuration.

In keeping with the invention, in one embodiment stent 30, as shown in FIGS. 4-12, is in the form of a tubular member for delivery through the vascular system and, for example, the coronary arteries. Stent 30 includes cylindrical rings 34 that are connected together to form the stent. The cylindrical rings 34 typically are short, on the order of approximately 0.85 mm to about 1.5 mm in length, and preferably there are from four to twenty cylindrical rings in a typical stent. The length of the rings and the number of rings per stent can vary to suit a particular application. Each ring 34 has a distal end 36 and a proximal end 38 and is formed of continuous undulations with peaks 40 configured as U-shaped elements 42. The peaks 40, also referred to as crests, curved portions, or irregular curved portions, can have many shapes including U-shapes, V-shapes, C-shapes, or irregular radii-of-curvature-shapes. The curvature formed on the proximal end 38 is sometimes referred to as "valleys" since the downward extending undulation forms a "depression" or valley along the ring. This is in contrast to the upward extending undulation of the ring on the distal end 36 which forms an "apex" or peak 40. When the peaks and valleys of the adjacent rings are arranged as is shown in FIGS. 6 and 11, i.e., the peaks 40 on each ring align with peaks 40 on adjacent rings, and likewise, valleys align with valleys, the rings are said to be "in phase." This is a term of art well known in the field. When the peaks 40 of one ring are aligned with valleys of an adjacent ring, as is depicted, for example, in FIGS. 5, 13 and 14, the rings are said to be "out of phase" or "not in phase." Each of the peaks 40 are connected to a first strut 44 and a second strut 46 to form the continuous cylindrical ring of undulations or U-shaped elements 42.

In further keeping with the invention, and with reference to FIGS. 4-12, the cylindrical rings 34 are aligned along the longitudinal axis of the stent and connected by one or more links 48. In this embodiment, the links 48 extend from one cylindrical ring to an adjacent cylindrical ring to connect the rings as well as maintain spacing between the rings. The links 48 are integrated into the second strut 46 so that there is a bar arm 50 that is a portion of second strut 46, and a link arm 52 that comprises a portion of link 48. By integrating the links 48 into the second strut 46, the distance between rings is optimized where it is desired to have a minimum space between the rings without the rings actually contacting each other. By insuring a minimum space between the rings the stent will provide maximum scaffolding in the vessel, and in the case of a drug coated stent will more evenly distribute the drug to the vessel. Further, by integrating the links into the second struts, the links can be made longer to increase flexibility yet maintain the minimum spacing between rings to ensure good scaffolding of the vessel and uniform drug delivery. Thus, links 48 are integrated into second struts 46, which creates gap 54 between the bar arm 50 and the link arm 52. When the stent is compressed onto the balloon portion of a catheter (see FIG. 1), gap 54 is necessarily small so that the bar arm 50 and the link arm 52 are substantially parallel to each other and substantially parallel to the longitudinal axis of the stent. As the stent is expanded, as shown in FIGS. 6 and 11, the gap 54 is substantially greater than when the stent is in a compressed configuration when being delivered on the balloon catheter to the target site. Preferably, the gap 54 widens as the stent is expanded by bending at curved portion 56 which is where link arm 52 terminates into bar arm 50.

The embodiment shown in FIG. 6 is more suitable to stents formed from a superelastic alloy than for those that are balloon expandable and made from alloys that plastically deform (e.g., stainless steel, cobalt-chromium, tantalum, etc.). The angle of the links in FIG. 6 relative to an adjacent strut 59 is shown as 37°. This expansion angle can only be achieved through a heat set process during stent expansion when the stent is being made. Further, the expansion angle of 37° creates an offset "D" from one cylindrical ring to an adjacent cylindrical ring. The offset improves scaffolding of the stent so there is minimal unsupported surface area. The length of offset D can vary significantly depending upon factors such as the expansion angle, the dimensions of the stent, and the degree of heat set in the links. In one embodiment, D can range in length from about 0.0125 mm to about 0.0350 mm. In one preferred embodiment, D is approximately 0.0298 mm. Thus, the expansion characteristics shown in FIG. 6 are better suited for a stent made from a superelastic alloy. The expansion angle of 37° can be varied to suit a particular need and can range from about 60° (see FIG. 5) to about 30°.

Figure 13:
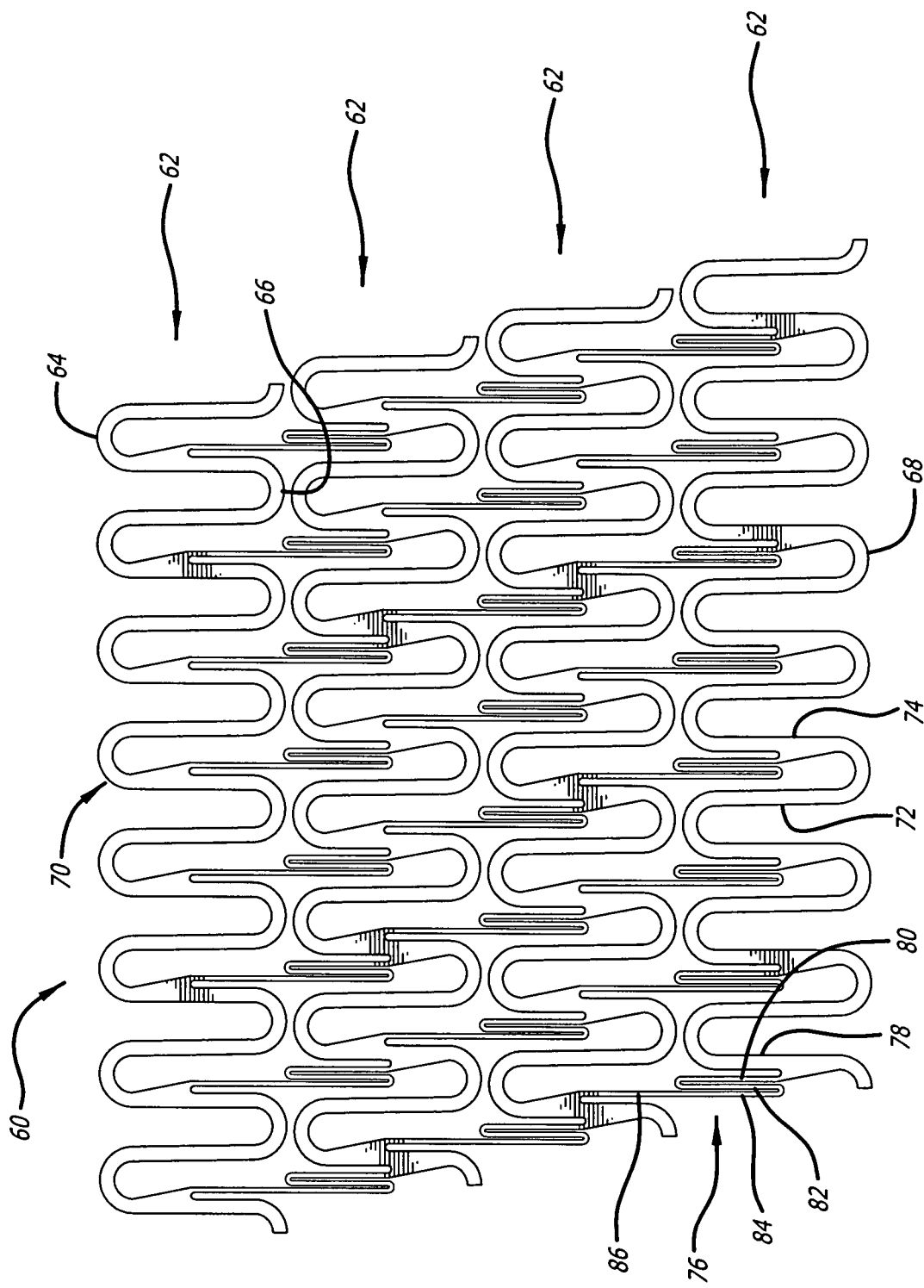
FIG. 13 is a plan view of one embodiment of the stent depicting links having undulating portions.
Figure 14:
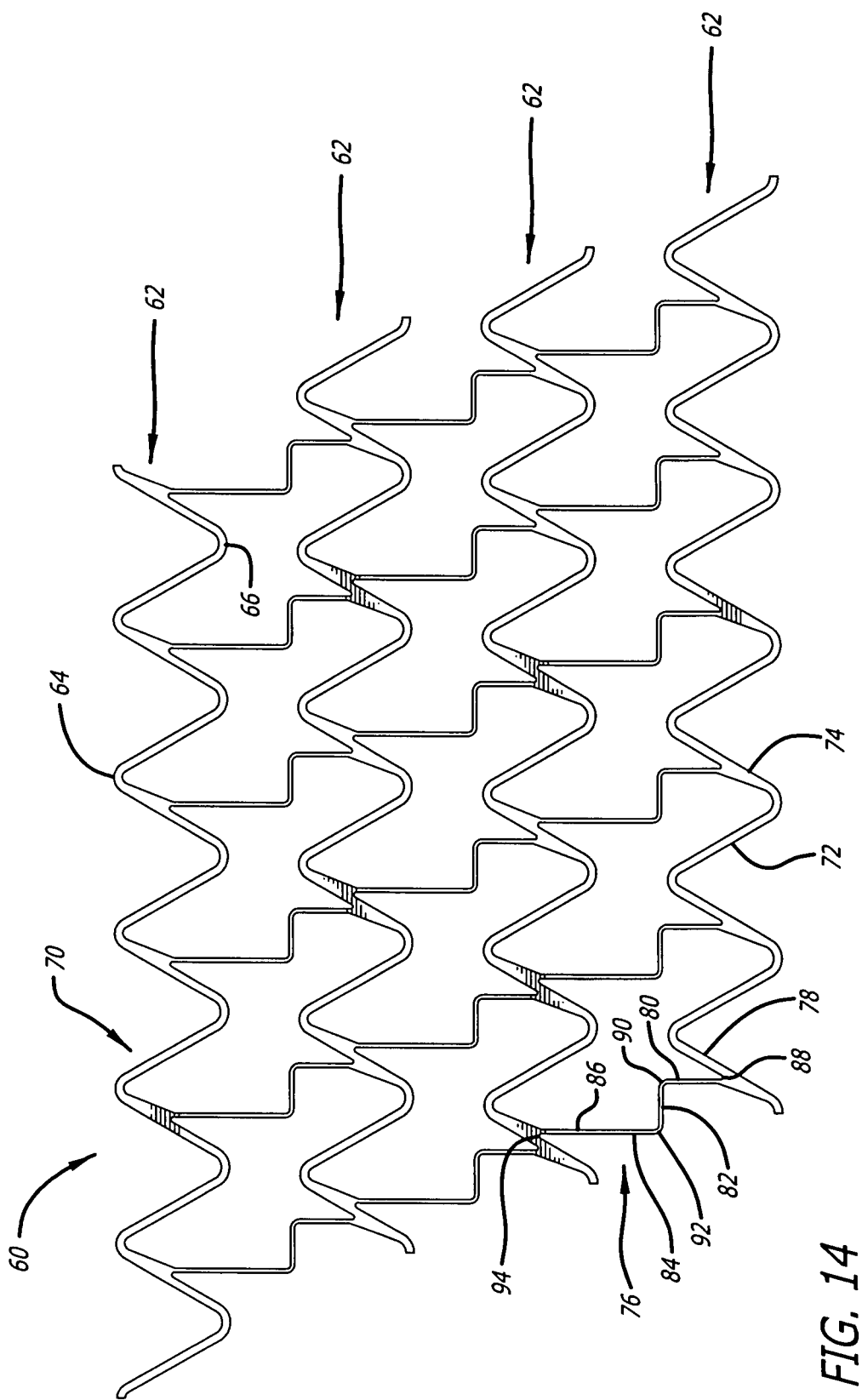
FIG. 14 is a plan view of the stent of FIG. 13 depicting schematically the stent in an expanded configuration.
Figure 15:
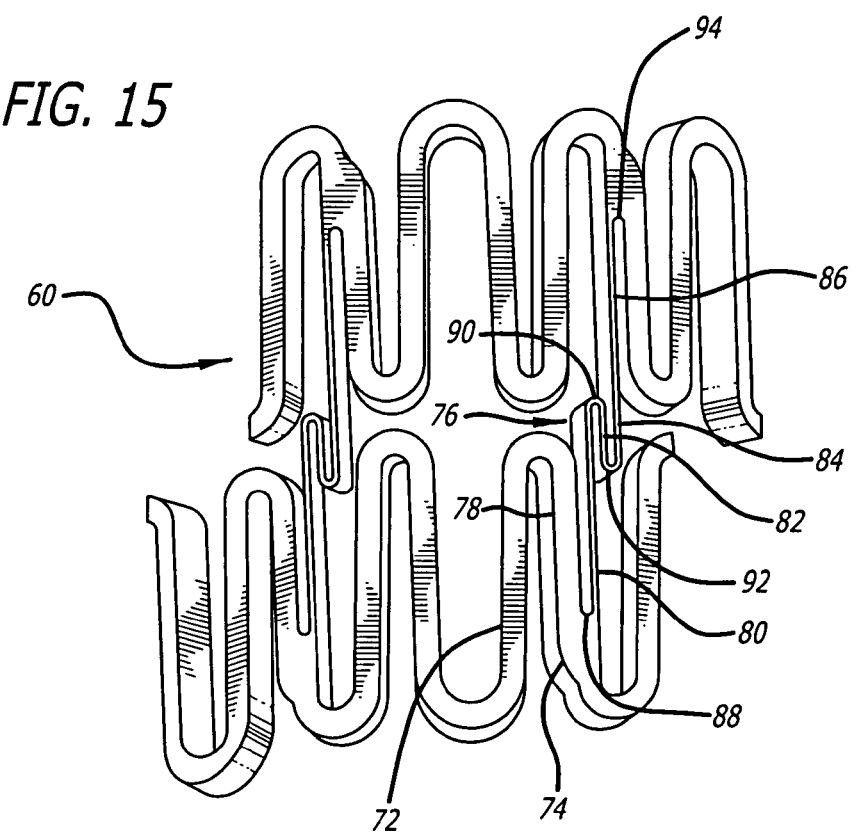
FIG. 15 is a partial plan view of the stent of FIG. 13 showing the undulating portions of the links.

In another embodiment of the invention, with reference to FIGS. 13-15, stent 60 is shown in a flattened condition, however, in use it is in a tubular configuration for use in the vascular system, for example in the peripheral or coronary arteries. The stents shown in FIGS. 13-15 have S-shaped or curved links and are more suitable for self-expanding stent applications, although the stents also can be balloon expandable. Stent 60 includes cylindrical rings 62 that are short, and on the order of approximately 0.85 mm to about 2.5 mm in length, and preferably stent 60 has between four and thirty cylindrical rings to treat a section of a peripheral or coronary artery. The length of the rings and the number of the rings for each stent can vary to suit a particular application. The lengths of the rings for use in the coronary arteries typically will be shorter than those used in peripheral arteries. Each ring 62 has a distal end 64 and a proximal end 66 and is formed of continuous undulations with peaks or crests 68 configured as U-shaped elements 70. The peaks 68 also can have other shapes including U shapes, V shapes, C shapes, or irregular radii of curvature shapes. Each of the peaks 68 are connected to a first strut 72 and a second strut 74 to form the continuous cylindrical ring of undulations or U-shaped elements 70.

In further reference to FIGS. 13-15, the cylindrical rings 62 are aligned along the longitudinal axis of the stent and connected by one or more S-shaped links 76. In this embodiment, the S-shaped links 76 extend from one cylindrical ring to an adjacent cylindrical ring to connect the rings as well as maintain the minimal spacing between the rings. The S-shaped links are integrated into the second strut 74 so that there is a bar arm 78 that is a portion of the second strut 74, and a first link arm 80, second link arm 82, third link arm 84, and fourth link arm 86, that comprise a portion of the S-shaped link 76. By integrating the S-shaped links 76 into the second strut 74, the distance between the rings is optimized where it is desired to have minimum spacing between the rings without the rings contacting each other. By insuring the minimum spacing between the rings, the stent will provide maximum scaffolding in the vessel, and in the case of a drug-coated stent, will more evenly distribute drugs to the vessel, including the peripheral and coronary arteries. Further, by integrating the links into the second struts, the links can be made longer in order to increase flexibility yet maintain the minimum spacing between the rings to ensure good scaffolding of the vessel and for providing uniform drug delivery. In the compressed configuration as shown in FIG. 13, the S-shaped links 76 are tightly packed or compressed between the rings so that the stent has an overall low profile and the stent is compressed inside of a catheter for self-expanding stents or crimped onto the balloon portion of a catheter for balloon expandable stents (not shown).

In one embodiment, the stent in FIGS. 13-15 is formed from a superelastic alloy such as nitinol. In this embodiment, when the stent is delivered into a vessel or coronary artery, it self-expands so that the second link arm 82 will turn inwardly approximately 90° as shown in FIG. 14. As the second link arm 82 turns inwardly, it will have a tendency to add length along the longitudinal axis of the stent which makes up for the foreshortening of the cylindrical rings as they expand radially outwardly. Referring to the S-shaped links as shown in FIG. 14, a first curved portion 88, a second curved portion 90, a third curved portion 92, and a fourth curved portion 94 further comprise the S-shaped links 76. Each of the curved portions open up as the stent self-expands from the compressed or crimped configuration of FIG. 13 to the expanded configuration of FIG. 14. Since the second link arm 82 expands to almost 90°, the length of the stent will remain approximately the same in both the crimped or compressed configuration and the deployed or expanded configuration when implanted in a coronary artery.

Another embodiment of the stent 60 having an S-shaped link 76 is shown in FIG. 15. In this embodiment, the length of the first link arm 80, second link arm 82, third link arm 84, and fourth link arm 86 is slightly different and shorter than that depicted in FIGS. 13 and 14. The length of the link arms, and the bar arm 78 can vary to suit a particular need, keeping in mind that one goal is to minimize the distance between cylindrical rings and to maintain the highly flexible nature of the stent along the longitudinal axis.

Figure 16:
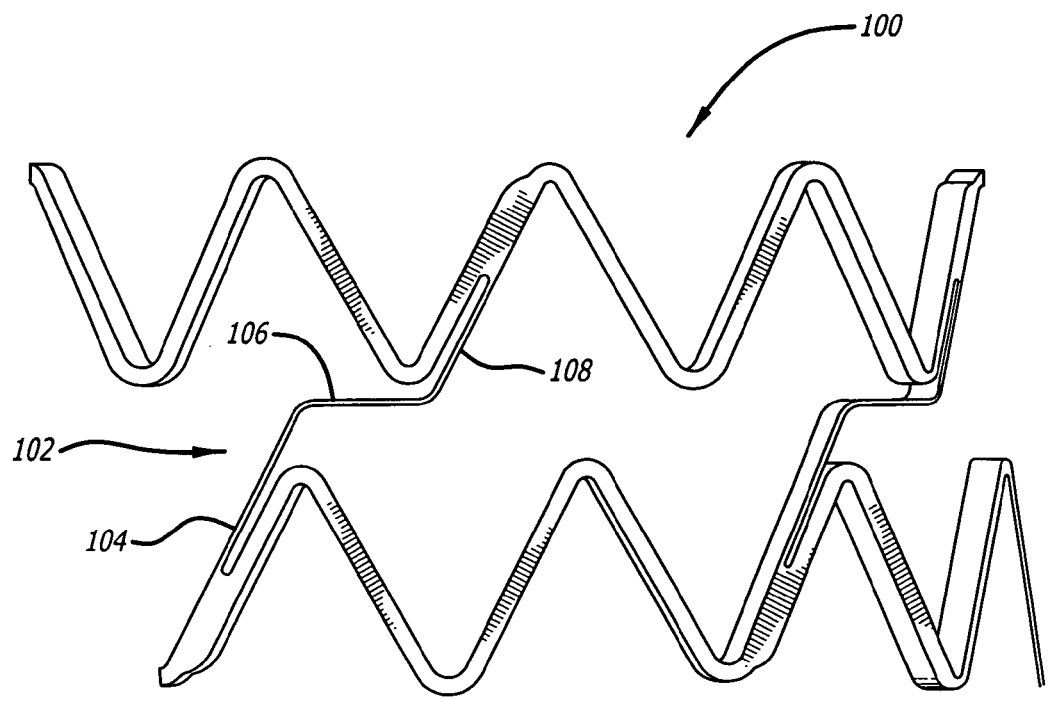
FIG. 16 is a partial plan view of another embodiment of the stent in which the links have at least on curve or bend to enhance flexibility.

In another embodiment as shown in FIG. 16, stent 100 is substantially the same as previously described with the exception of curved link 102. Curved link 102 is comprised of a first link arm 104, a second link arm 106, and a third link arm 108 which, as shown, expand so that second link arm 106 is approximately 90° to the longitudinal axis when the stent is expanded. When second link arm 106 expands to approximately 90°, the stent lengthens which makes up for the foreshortening, if any, of the cylindrical rings upon expansion. The stent shown in FIG. 16 functions substantially the same as those in the prior-described embodiments.

Figure 17:
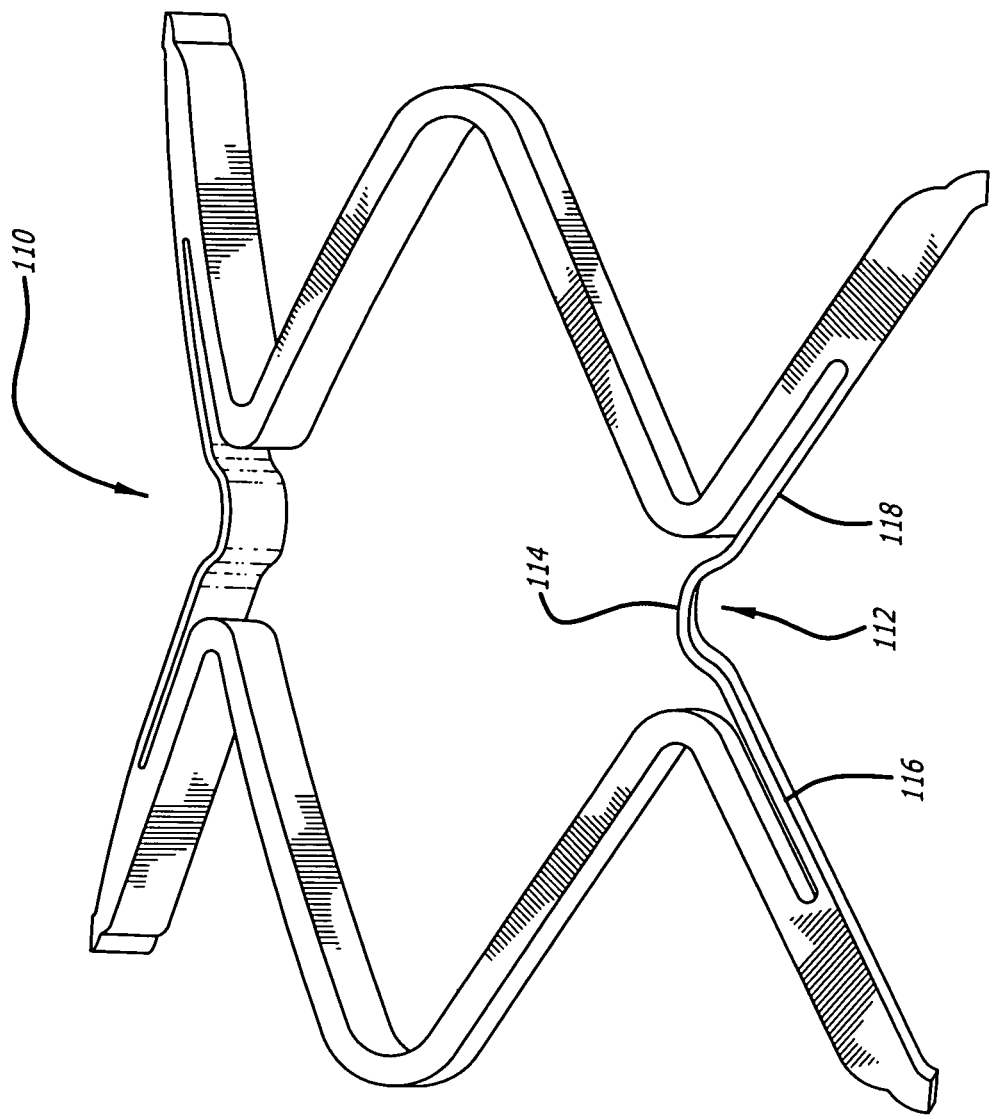
FIG. 17 is a partial enlarged plan view of one embodiment of the stent in which the links have a curve or bend in order to enhance flexibility.

With respect to FIG. 17, stent 110 includes C-shaped link 112 having a first bend portion 114 and a first link arm 116 and a second link arm 118. During expansion of the stent 110, the first bend portion 114 expands thereby lengthening the stent in the longitudinal direction and compensating for any foreshortening of the cylindrical rings as they expand radially outwardly. The stent disclosed in FIG. 17 operates substantially the same as that described in the prior embodiments.

The stent of the present invention can be made from a metallic material or an alloy such as, but not limited to, cobalt chromium alloy (ELGILOY), stainless steel (316L), MP35N, MP20N, ELASTINITE, nitinol, tantalum, nickel-titanium alloy, platinum-iridium alloy, gold, magnesium, or combinations thereof. MP35N and MP20N are trade names for alloys of cobalt, nickel, chromium and molybdenum available from Standard Press Steel Co., Jenkintown, Pa. MP35N consists of 35% nickel, 20% chromium, and 120% molybdenum. MP20N consists of 50% cobalt, 20% nickel, 20% chromium, and 20% molybdenum. Stents also can be made from bioabsorbable or biostable polymers.

Any of the stents disclosed herein can be coated with a drug for treating the vascular system. The drug, therapeutic substance or active agent, terms which are used interchangeably, in the coating can inhibit the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect for a diseased condition. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich, Inc., Milwaukee, Wis.; or COSMEGEN available from Merck & Co., Inc., Whitehorse Station, N.J.). Synonyms of actinomycin D include dactinomycin, actinomycin IV, actinomycin $I_1$, actinomycin $X_1$, and actinomycin $C_1$. The actve agent can also fall under the genus of antineoplastic, anti-inflammatory, antiplatelet, anticoagulant, antifibrin, antithrombin, antimitotic, antibiotic, antiallergic and antioxidant substnaces. Examples of such antineoplastics and/or antimitotics include paclitaxel (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co.). Examples of such antiplatelets, anticoagulants, antifibrin, and antithrombins include sodium heparin, low molecular weight heparins, heparinoids, hirudin, argatroban, forskolin, vapiprost, pro-arg-chloromethylketone (synthetic antithrombin), dipyridamole, flycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co.), cilazapril or lisinopril (e.g., Prinvil® and Prinzide® from Merck & Co., Inc.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and it derivatives and analogs, and dexamethasone.

Coating 20 can be made from any suitable biocompatible polymer, examples of which include ethylene vinyl alcohol copolymer (commonly known by the generic name EVOH or by the trade name EVAL); poly(hydroxyvalerate); poly(L-lactic acid); polycaprolactone; poly(lactide-co-gly-colide); poly(hydroxybutyrate); poly(hydroxybutyrate-co-valerate); polydioxanone; polyorthoester; polyanhydride; poly(glycolic acid); poly(D,L-lactic acid); poly(flycolic acid-co-trimethylene carbonate); polyphosphoester; poly-phosphoester urethane; poly(aminoacids); cyanoacrylates; poly(trimethylene carbonate); poly(iminocarbonate); copoly(ether-esters) (e.g., PEO/PLA); polyalkylene oxalates; poly-phosphazenes; biomolecules, such as fibrin, fibrinogen, cellulose, starch, collagen and hyaluronic acid; polyurethanes; silicones; polyesters; polyolefiins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones, polyvinyl aromatics, such as polystyrene; polyvinyl esters, such as polyvinyl acetate; copolymers of vinyl monomers with each other and olefins, such as ethylenemethyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose. Coating 20 can also be silicon foam, neoprene, santoprene, or closed cell foam.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials and coatings described herein are intended to define the parameters of the invention, they are by no means limiting and are exemplary embodiments.

What is claimed:

1. A stent, comprising:
    a tubular member having a plurality of rings spaced apart along a longitudinal axis, each ring having a distal end and a proximal end, each ring having a first delivery position and a second expanded position;
    the rings having curved portions forming a plurality of distally-extending peaks and a plurality of proximally-extending peaks, the distally-extending peaks and the proximally-extending peaks being connected by first struts and second struts, the second strut having a width which tapers from a first width to a second, larger width, wherein adjacent distally-extending peaks are spaced apart to define a space therebetween when the rings are in the first delivery position, the space extending from a first strut and second strut on each ring to the ends of the adjacent distally-extending peaks; and
    a plurality of S-shaped links for connecting adjacent cylindrical rings, a portion of the S-shaped links being integrally formed from a portion of the second struts, each of the S-shaped links extending from the larger width of the second strut, wherein a portion of the second struts splits into a first link arm and a bar arm, the first link arm being separated from the bar arm by a gap, each S-shaped link including a second link arm and a third link arm, the first, second and third link arms being connected together and placed in a side-by-side relationship and at least a portion of each of the first, second and third link arms is located within the above-defined space when the rings are placed in the first delivery position.

2. The stent of claim 1, wherein the stent includes a drug coating.

3. The stent of claim 1, wherein the S-shaped links connect adjacent rings by extending from the second strut of one ring to the second strut of an adjacent ring.

4. The stent of claim 1, wherein the first struts have a first width and the second struts have a second width, the first width being less than the second width.

5. The stent of claim 4, wherein the second width of the second struts is defined by a width of the link plus a width of the gap plus a width of the link arm.

6. The stent of claim 5, wherein the first width of the first struts is approximately equal to the width of link arm of the second struts.

7. The stent of claim 1, wherein each of the first, second and third link arms is substantially parallel to each other when the rings are in the first delivery position.

8. The stent of claim 1, wherein each of the first link arms remains substantially parallel to the first link arms on the same ring and adjacent rings when the rings are in the second expanded position.

9. The stent of claim 1, wherein the links connect adjacent rings by extending from the second strut of one ring to the second strut of an adjacent ring.

10. The stent of claim 1, wherein each of the first, second and third link arms are located adjacent to the bar arm when the rings are in the first delivery position.

11. The stent of claim 1, wherein each of the second link arms are located between adjacent rings when the rings are in the first delivery position.

12. The stent of claim 11, wherein each of the second link arms is shorter than the first and third link arms.

13. The stent of claim 1, wherein the second, larger strut width of each second strut is located at the area where the second strut splits into the first link arm and the bar arm.

14. A stent, comprising:
    a tubular member having a plurality of rings spaced apart along a longitudinal axis, each ring having a distal end and a proximal end, each ring having a first delivery position and a second expanded position;
    the rings having curved portions forming a plurality of distally-extending peaks and a plurality of proximally-extending peaks, the distally-extending peaks and the proximally-extending peaks being connected by first struts and second struts, the first strut having a width and the second strut having a width which tapers from a first width to a second, larger width, wherein adjacent distally-extending peaks are spaced apart to define a space therebetween when the rings are in the first delivery position, the space extending from a first strut and second strut on each ring to the ends of the adjacent distally-extending peaks; and a plurality of S-shaped links for connecting adjacent cylindrical rings, a portion of the S-shaped links being integrally formed from a portion of the second struts, each of the S-shaped links extending from the larger width of the second strut, each of S-shaped links having a particular length to maintain the rings spaced a certain distance apart when the rings are in the first delivery position and an expanded length to move the rings further apart from each other when the rings are placed in the second expanded position and at least a portion of each of the first, second and third link arms is located within the above-defined space when the rings are placed in the first delivery position.

15. The stent of claim 14, wherein a portion of the second struts splits into a first link arm and a bar arm, the first link being separated from the bar arm by a gap.

16. The stent of claim 15, wherein each S-shaped link includes a second link arm and a third link arm, the first, second and third link arms being connected together and placed in a side-by-side relationship when the rings are placed in the first delivery position.

17. The stent of claim 16, wherein one of the first, second and third link arm has a length which is different from the other link arms.

18. The stent of claim 16, wherein at least two of the first, second and third link arms has substantially the same length.

19. The stent of claim 16, wherein each of the first, second and third link arms are located adjacent to the bar arm when the rings are in the first delivery position.

20. The stent of claim 16, wherein each of the second link arms are located between adjacent rings when the rings are in the first delivery position.

21. The stent of claim 16, wherein each of the second link arms is shorter than the first and third link arms.

22. The stent of claim 16, wherein each of the third link arms is coupled to an adjacent ring.

23. The stent of claim 14, wherein each of the S-shaped links form an S-shape when the rings are in both the first delivery position and the second expanded position.

24. A stent, comprising:
a tubular member having a plurality of rings spaced apart along a longitudinal axis, each ring having a distal end and a proximal end, each ring having a first delivery position and a second expanded position;
the rings having curved portions forming a plurality of distally-extending peaks and a plurality of proximally-extending peaks, the distally-extending peaks and the proximally-extending peaks being connected by first struts and second struts, the second strut having a width which tapers from a first width to a second, larger width, the rings being out of phase when the rings are either in the first delivery position or the second expanded position, wherein adjacent distally-extending peaks are spaced apart to define a space therebetween when the rings are in the first delivery position, the space extending from a first strut and second strut on each ring to the ends of the adjacent distally-extending peaks; and a plurality of S-shaped links connecting adjacent cylindrical rings together, the S-shaped links being integrally formed from a portion of the second struts, each of the S-shaped links extending from the larger width of the second strut, wherein a portion of the second struts splits into a first link arm and a bar arm, the first link arm being separated from the bar arm by a gap, each S-shaped link including a second link arm and a third link arm, the first, second and third link arms being connected together and placed in a side-by-side relationship and at least a portion of each of the first, second and third link arms is located within the above-defined space when the rings are placed in the first delivery position.

25. The stent of claim 24, wherein the rings are out of phase in both the first delivery position and the second expanded position.

26. The stent of claim 24, wherein the second, larger strut width of each second strut is located at the area where the second strut splits into a first link arm and a bar arm.

27. A stent, comprising:
a tubular member having a plurality of rings spaced apart along a longitudinal axis, each ring having a distal end and a proximal end, each ring having a first delivery position and a second expanded position;
the rings having curved portions forming a plurality of distally-extending peaks and a plurality of proximally-extending peaks, the distally-extending peaks and the proximally-extending peaks being connected by first struts and second struts, the second strut having a width which tapers from a first width to a second, larger width, wherein adjacent distally-extending peaks are spaced apart to define a space therebetween when the rings are in the first delivery position, the space extending from a first strut and second strut on each ring to the ends of the adjacent distally-extending peaks; and a plurality of S-shaped links for connecting adjacent cylindrical rings, a portion of the S-shaped links being integrally formed from a portion of the second struts, each of the S-shaped links extending from the larger width of the second strut, each of S-shaped links having a collapsed S-shape configuration when the rings are in the first delivery position and a seconded expanded S-shape configuration when the rings are in the second expanded position and at least a portion of each of the first, second and third link arms is located within the above-defined space when the rings are placed in the first delivery position.

28. The stent of claim 27, wherein the second, larger strut width of the second strut area is located at the area where the second strut splits into a first link arm and a bar arm.

29. The stent of claim 27, wherein a portion of the second struts splits into a first link arm and a bar arm, the first link arm being separated from the bar arm by a gap.

30. The stent of claim 29, wherein each S-shaped link includes a second link arm and a third link arm, the first, second and third link arms being connected together and placed in a side-by-side relationship when the rings are placed in the first delivery position.

31. The stent of claim 30, wherein each of the first, second and third link arms are located adjacent to the bar arm when the rings are in the first delivery position.

* * * * *